United States Patent
Yamamoto et al.

(10) Patent No.: US 11,510,427 B2
(45) Date of Patent: Nov. 29, 2022

(54) FOOD AND BEVERAGES CONTAINING CYCLO(ASPARTYL-GLYCINE), GLUCOSE, AND MALTOSE

(71) Applicant: SUNTORY HOLDINGS LIMITED, Osaka (JP)

(72) Inventors: Kenji Yamamoto, Kyoto (JP); Wakana Taguchi, Kanagawa (JP); Hideki Matsubayashi, Kanagawa (JP)

(73) Assignee: SUNTORY HOLDINGS LIMITED, Osaka (JP)

( * ) Notice: Subject to any disclaimer, the term of this patent is extended or adjusted under 35 U.S.C. 154(b) by 565 days.

(21) Appl. No.: 16/471,742

(22) PCT Filed: Dec. 18, 2017

(86) PCT No.: PCT/JP2017/045235
§ 371 (c)(1),
(2) Date: Jun. 20, 2019

(87) PCT Pub. No.: WO2018/117000
PCT Pub. Date: Jun. 28, 2018

(65) Prior Publication Data
US 2019/0328015 A1    Oct. 31, 2019

(30) Foreign Application Priority Data

Dec. 21, 2016    (JP) .............................. JP2016-247615

(51) Int. Cl.
| | | |
|---|---|---|
| *A23L 27/30* | (2016.01) | |
| *A23L 27/21* | (2016.01) | |
| *A23L 27/00* | (2016.01) | |
| *A23F 3/40* | (2006.01) | |
| *A23L 2/60* | (2006.01) | |

(52) U.S. Cl.
CPC .............. *A23L 27/33* (2016.08); *A23F 3/405* (2013.01); *A23L 2/60* (2013.01); *A23L 27/21* (2016.08); *A23L 27/84* (2016.08); *A23V 2002/00* (2013.01)

(58) Field of Classification Search
CPC .......... A23L 27/33; A23L 27/21; A23L 27/84; A23L 2/60; A23F 3/405; A23V 2002/00
USPC .......................... 426/534, 580, 590, 583, 634
See application file for complete search history.

(56) References Cited

U.S. PATENT DOCUMENTS

| | | |
|---|---|---|
| 5,144,073 A | 9/1992 | Hubbs |
| 2011/0159145 A1 | 6/2011 | Alho-Lehto et al. |
| 2012/0283178 A1 | 11/2012 | Tsuruoka et al. |
| 2013/0183404 A1 | 7/2013 | Whalen |
| 2017/0114030 A1 | 4/2017 | Suzuki et al. |
| 2017/0129919 A1 | 5/2017 | Suzuki et al. |

FOREIGN PATENT DOCUMENTS

| | | |
|---|---|---|
| EP | 2 462 812 A1 | 6/2012 |
| JP | 2012-517998 A | 8/2012 |
| WO | 2015/194070 A1 | 12/2015 |
| WO | 2015/194205 A1 | 12/2015 |

OTHER PUBLICATIONS

Extended Search Report dated Jul. 23, 2020, issued in counterpart Application No. 17882885.1 (6 pages).
Samanen, James et al., "Chemical Approaches to Improve the Oral Bioavailability of Peptidergic Molecules", Journal of Pharmacy and Pharmacology, John Wiley & Sons Ltd., Feb. 1, 1996, vol. 48, pp. 119-135; Cited in EESR dated Jul. 23, 2020.
Office Action dated May 9, 2020, issued in counterpart SG Application No. 11201905623Y (9 pages).
Ishibashi, Norio et al., "A Mechanism for Bitter Taste Sensibility in Peptides", Agric. Biol. Chem., 1988, vol. 52, No. 3, pp. 819-827; Cited in SG Office Action dated May 9, 2020.
International Search Report dated Mar. 20, 2018, issued in counterpart application No. PCT/JP2017/045235 (2 page).
Prasad, "Bioactive Cyclic Dipeptides", Peptides, 1995, vol. 16, No. 1, pp. 151-164, cited in the specification (14 pages).
Borthwick, "2,5-Diketopiperazines: Synthesis, Reactions, Medicinal Chemistry, and Bioactive Natural Products", Chemical Reviews, 2012, 112, pp. 3641-3716, cited in the specification (39 pages).

*Primary Examiner* — Leslie A Wong
(74) *Attorney, Agent, or Firm* — WHDA, LLP

(57) ABSTRACT

Provided is a food or beverage product having good taste with sharp astringent taste of cycloaspartylglycine in the food or beverage product reduced. The content of cycloaspartylglycine and the weight ratio of the content of glucose to the content of maltose ([glucose]/[maltose] weight ratio) in the food or beverage product are adjusted to fall within specific ranges.

19 Claims, No Drawings

FOOD AND BEVERAGES CONTAINING CYCLO(ASPARTYL-GLYCINE), GLUCOSE, AND MALTOSE

This application is a 371 of PCT/JP2017/045235 filed Dec. 18, 2017.

TECHNICAL FIELD

The present invention relates to a food or beverage product containing cycloaspartylglycine, glucose, and maltose, more specifically, to a food or beverage product wherein a content of cycloaspartylglycine falls within a specific range and a weight ratio of a content of glucose to a content of maltose ([glucose]/[maltose] weight ratio) falls within a specific range, a method for producing the food or beverage product, and a method for reducing sharp astringent taste of the cycloaspartylglycine in the food or beverage product.

BACKGROUND ART

"Dipeptides" in which two amino acids are bound are gaining attention as functional substances. Physical or chemical properties which are not present in single amino acids or new functions can be added to such dipeptides, and thus they are expected to have application ranges beyond single amino acids.

In recent years, a diketopiperazine derivative which is a cyclic dipeptide having a cyclic structure formed by dehydration condensation of an amino group present at the terminal of a dipeptide and a carboxyl group has been developed. The cyclic dipeptide is reported to have various physiological activities, and the demand thereof is expected to expand in the medical and pharmacological fields. For example, it is reported in PTL 1 that a cyclic dipeptide having a 2,5-diketopiperazine structure has antidepressant activity, learning motivation improving activity, and the like. Further, NPL 1 discloses that cyclohistidylproline [Cyclo(His-Pro)] exhibits many physiological activities such as central nervous system activities, e.g., decreasing the body temperature and suppressing appetite, and hormone-like activities e.g., suppressing prolactin secretion and promoting growth hormone secretion. Further, NPL 2 discloses that cyclotryptophanylproline [Cyclo(Trp-Pro)] exhibits anticancer activity, cyclohistidylproline [Cyclo(His-Pro)] and cycloglycylproline [Cyclo(Gly-Pro)] exhibit antibacterial activity, cyclohistidylproline [Cyclo(His-Pro)] exhibits neuroprotective activity, and cycloglycylproline [Cyclo(Gly-Pro)] exhibits memory function improving activity.

CITATION LIST

Patent Literature

PTL 1: Japanese Translation of PCT International Application Publication No. 2012-517998 T

Non Patent Literature

NPL 1: Peptides, 16 (1), 151-164 (1995)
NPL 2: Chemical Reviews, 112, 3641-3716 (2012)

SUMMARY OF INVENTION

Technical Problem

As described above, cyclic dipeptides have various physiological activities. For example, cycloaspartylglycine has TRPV1-stimulating activity and obesity-preventing and improving activity, as described in PCT/JP2016/070639 and PCT/JP2016/070864. Meanwhile, cycloaspartylglycine has sharp astringent taste. Therefore, development of a method for reducing sharp astringent taste of cycloaspartylglycine to produce an easy-to-take food or beverage product is desired.

It is an object of the present invention to provide a food or beverage product having good taste with sharp astringent taste of cycloaspartylglycine in the food or beverage product reduced.

Solution to Problem

First, the inventors have found that, in the case of using cycloaspartylglycine alone for a food or beverage product, the food or beverage product cannot be favorably taken due to its sharp astringent taste. However, the inventors have found surprisingly that the sharp astringent taste of cycloaspartylglycine is reduced in a food or beverage product containing a certain amount of cycloaspartylglycine by adjusting a [glucose]/[maltose] weight ratio in the food or beverage product to fall within a specific range. Further, they have found also that the food or beverage product has a favorable balance between appropriate astringent taste unique to cycloaspartylglycine and sweetness derived from glucose, maltose, and the like, thereby accomplishing the present invention.

That is, the present invention relates to the following but is not limited thereto.

(1) A food or beverage product comprising cycloaspartylglycine, glucose, and maltose, wherein
a content of cycloaspartylglycine in the food or beverage product is 0.0020 to 7.5 mg/100 mL, and
a weight ratio of the content of glucose to the content of maltose ([glucose]/[maltose] weight ratio) in the food or beverage product is 0.005 to 15.
(2) The food or beverage product according to (1), wherein the content of cycloaspartylglycine is 0.0080 to 3.0 mg/100 mL.
(3) The food or beverage product according to (1) or (2), wherein the [glucose]/[maltose] weight ratio in the food or beverage product is 0.08 to 7.0.
(4) The food or beverage product according to any of (1) to (3), wherein the content of cycloaspartylglycine (mg/100 mL) (X) and the [glucose]/[maltose] weight ratio (Y) in the food or beverage product satisfy $Y \leq 11.02 \times X^{-0.154}$ and $Y \geq 0.0255 \times X^{0.7454}$.
(5) The food or beverage product according to any of (1) to (4), wherein the content of cycloaspartylglycine (mg/100 mL) (X) and the [glucose]/[maltose] weight ratio (Y) in the food or beverage product satisfy $Y \leq 6.6445 \times X^{-0.091}$ and $Y \geq 0.49 \times X^{0.7837}$.
(6) The food or beverage product according to any of (1) to (5), wherein the cycloaspartylglycine is added as a heat-treated product of animal or plant-derived peptide.
(7) The food or beverage product according to (6), wherein the heat-treated product of animal or plant-derived peptide is obtained from soybean peptide, tea peptide, whey peptide, or collagen peptide.
(8) The food or beverage product according to any of (1) to (7), wherein the food or beverage product is a tea beverage.
(9) The food or beverage product according to (8), wherein the food or beverage product is a blended tea beverage.
(10) The food or beverage product according to any of (1) to (9), wherein the food or beverage product is packaged in a container.

(11) A method for producing a food or beverage product, comprising:
   step (a) of adding cycloaspartylglycine to adjust a content of cycloaspartylglycine in the food or beverage product to 0.0020 to 7.5 mg/100 mL; and
   step (b) of adding glucose and maltose to adjust a weight ratio of the content of glucose to the content of maltose ([glucose]/[maltose] weight ratio) in the food or beverage product to 0.005 to 15.

(12) The production method according to (11), wherein the content of cycloaspartylglycine adjusted in step (a) is 0.0080 to 3.0 mg/100 mL.

(13) The production method according to (11) or (12), wherein the [glucose]/[maltose] weight ratio in the food or beverage product adjusted in step (b) is 0.08 to 7.0.

(14) A method for reducing sharp astringent taste of cycloaspartylglycine in a food or beverage product, comprising:
   step (a) of adding cycloaspartylglycine to adjust a content of cycloaspartylglycine in the food or beverage product to 0.0020 to 7.5 mg/100 mL; and
   step (b) of adding glucose and maltose to adjust a weight ratio of the content of glucose to the content of maltose ([glucose]/[maltose] weight ratio) in the food or beverage product to 0.005 to 15.

(15) The method according to (14), wherein the content of cycloaspartylglycine adjusted in step (a) in the food or beverage product is 0.0080 to 3.0 mg/100 mL.

(16) The method according to (14) or (15), wherein the [glucose]/[maltose] weight ratio in the food or beverage product adjusted in step (b) is 0.08 to 7.0.

Advantageous Effects of Invention

The present invention can give a food or beverage product having good taste with sharp astringent taste unique to cycloaspartylglycine in the food or beverage product reduced. Further, the present invention can achieve a food or beverage product having favorable taste and good balance between appropriate astringent taste unique to cycloaspartylglycine and sweetness derived from glucose, maltose, and the like.

DESCRIPTION OF EMBODIMENTS

1. Food or Beverage Product

One embodiment of the present invention is a food or beverage product containing cycloaspartylglycine, glucose, and maltose, wherein a content of cycloaspartylglycine in the food or beverage product falls within a specific range and a weight ratio of a content of glucose to a content of maltose ([glucose]/[maltose] weight ratio) in the food or beverage product falls within a specific range. In this description, the "weight ratio of a content of glucose to a content of maltose" may be referred to simply as "[glucose]/[maltose] weight ratio".

1-1. Cycloaspartylglycine

Cycloaspartylglycine in the present invention is one of cyclic dipeptides and is a compound having a diketopiperazine structure formed by dehydration condensation of aspartic acid and glycine.

Cycloaspartylglycine in the present invention may be in the form of a pharmacologically acceptable salt (including inorganic salts and organic salts) such as sodium salt, potassium salt, calcium salt, magnesium salt, ammonium salt, hydrochloride, sulfate, nitrate, phosphate, and organic acid salts (such as acetate, citrate, maleate, malate, oxalate, lactate, succinate, fumarate, propionate, formate, benzoate, picrate, benzene sulfonate, and trifluoroacetate) of cycloaspartylglycine, but there is no limitation to these. Such a salt of cycloaspartylglycine can be easily prepared by those skilled in the art using any known method in the field. In this description, "cycloaspartylglycine or a salt thereof" may be collectively referred to simply as "cycloaspartylglycine".

Cycloaspartylglycine used in the present invention can be prepared according to a known method in the field. For example, it may be produced by a chemical synthesis method, an enzymatic method, or a microbial fermentation method, may be synthesized by dehydration and cyclization of linear aspartylglycine, or can be prepared according to the method described in Japanese Patent Application Laid-Open No. 2003-252896 or Journal of Peptide Science, 10, 737-737, 2004. For example, an animal or plant-derived peptide obtained by applying enzymatic treatment or heat treatment to a raw material containing an animal or plant-derived protein is further subjected to high-temperature heat treatment, so that a heat-treated product of the animal or plant-derived peptide rich in cycloaspartylglycine can be obtained. From these viewpoints, cycloaspartylglycine used in the present invention may be chemically or biologically synthesized or may be obtained from an animal or plant-derived peptide.

The content of cycloaspartylglycine in the food or beverage product of the present invention is not specifically limited, but when the content of cycloaspartylglycine is excessively large, favorable intake may be impossible due to excessively strong sharp astringent taste of cycloaspartylglycine. The lower limit of the content of cycloaspartylglycine in the food or beverage product of the present invention is 0.0020 mg (0.0020 mg/100 mL) or more, preferably 0.0025 mg/100 mL or more, more preferably 0.0080 mg/100 mL or more, furthermore preferably 0.010 mg/100 mL or more, with respect to 100 mL of the food or beverage product. Further, the upper limit of the content of cycloaspartylglycine in the food or beverage product of the present invention is preferably 8.1 mg/100 mL or less, more preferably 7.5 mg/100 mL or less, furthermore preferably 3.0 mg/100 mL or less, particularly preferably 2.7 mg/100 mL or less. Typically, the content range of cycloaspartylglycine in the food or beverage product of the present invention is 0.0020 to 8.1 mg/100 mL, preferably 0.0020 to 7.5 mg/100 mL, more preferably 0.0080 to 3.0 mg/100 mL, furthermore preferably 0.010 to 2.7 mg/100 mL.

The content of cycloaspartylglycine can be measured by a known method and can be measured, for example, by the LC-MS/MS method.

In the present invention, the method for adjusting the content of cycloaspartylglycine is not specifically limited, as long as the content of cycloaspartylglycine in the food or beverage product falls within the aforementioned ranges. For example, commercially available cycloaspartylglycine, synthetic cycloaspartylglycine that is produced by a chemical synthesis method, an enzymatic method, or a microbial fermentation method, or a heat-treated product of animal or plant-derived peptide rich in cycloaspartylglycine can be used. Further, only one of commercially available or synthetic products of cycloaspartylglycine, and a heat-treated product of animal or plant-derived peptide rich in cycloaspartylglycine can be used, or two or more of them can be used in combination.

A heat-treated product of animal or plant-derived peptide contains a wide variety of cyclic dipeptides other than cycloaspartylglycine. Therefore, in the case of adjusting the content of cycloaspartylglycine in the food or beverage product using such a heat-treated product of animal or plant-derived peptide, cyclic dipeptides other than cycloaspartylglycine are also added in the food or beverage product. However, in the present invention, the sharp astringent taste unique to cycloaspartylglycine is made noticeable, regardless of the content of other cyclic dipeptides, when the content of cycloaspartylglycine in the food or beverage product falls within a predetermined range, and the sharp astringent taste of cycloaspartylglycine is reduced, regardless of the content of other cyclic dipeptides, when the [glucose]/[maltose] weight ratio in the food or beverage product is adjusted to fall within a specific range.

1-2. Heat-Treated Product of Animal or Plant-Derived Peptide

In this description, the "animal or plant-derived peptide" is not specifically limited, but soybean peptide, tea peptide, malt peptide, whey peptide, and collagen peptide, for example, can be used therefor. Among these, soybean peptide and tea peptide are preferable in the present invention. An animal or plant-derived peptide prepared from a raw material containing an animal or plant-derived protein or a protein using a known method may be used, or a commercially available animal or plant-derived peptide may be used.

1-2-1. Soybean Peptide

In this description, "soybean peptide" refers to a low-molecular weight peptide obtained by applying enzymatic treatment or heat treatment to soy protein to lower the molecular weight of the protein. Any soybean (scientific name: *Glycine max*) can be used as a raw material with no limitation in variety and production area, and processed products such as a crushed product can be also used.

1-2-2. Tea Peptide

In this description, "tea peptide" refers to a low-molecular weight peptide derived from tea obtained by applying enzymatic treatment or heat treatment to a tea (including tea leaves or used tea leaves) extract to lower the molecular weight of the protein. As the tea leaves serving as a raw material to be extracted, portions that can be extracted for intake such as leaves and stems of tea produced from tea trees (scientific name: *Camellia sinensis*) can be used. Further, the form such as macrophyllous and powder forms is not limited. The harvest time of tea leaves can be also appropriately selected corresponding to the desired flavor.

1-2-3. Malt Peptide

In this description, "malt peptide" refers to a low-molecular weight peptide derived from malt obtained by applying enzymatic treatment or heat treatment to an extract obtained from malt or a ground product thereof to lower the molecular weight of the protein. Any malt peptide can be used as a raw material with no limitation in variety and production area, but barley malt obtained by germinating seeds of barley is particularly suitably used therefor. In this description, barley malt may be expressed simply as malt.

1-2-4. Whey Peptide

The raw material of whey peptide is not specifically limited, but examples thereof include WPC (Whey Protein Concentrate) and WPI (Whey Protein Isolate) which are whey proteins. Whey peptide refers to a product obtained by degrading such a whey protein with an enzyme or the like. The degree of degradation may vary, but when the degree of degradation is low, milk odor tends to be stronger, and the liquid after dissolution tends to be opaque (turbid). Meanwhile, when the degree of degradation is high, the liquid after dissolution tends to be transparent, but bitterness and astringency tend to increase.

1-2-5. Collagen Peptide

In this description, "collagen peptide" refers to a low-molecular weight peptide obtained by applying enzymatic treatment or heat treatment to collagen or a ground product thereof to lower the molecular weight of collagen. Collagen is a main protein for connective tissues of animals and is the most abundant protein in mammalian bodies including humans.

1-2-6. Heat-Treated Product of Animal or Plant-Derived Peptide

As described above, a heat-treated product of animal or plant-derived peptide rich in cycloaspartylglycine can be obtained by applying high-temperature heat treatment to an animal or plant-derived peptide. In this description, the "high-temperature heat treatment" is treatment for a certain time at a temperature of 100° C. or more and a pressure over the atmospheric pressure. As a high-temperature and high-pressure treatment device, a pressure resistant extractor, a pressure cooker, an autoclave or the like can be used corresponding to the conditions.

The temperature in the high-temperature heat treatment is not specifically limited, as long as it is 100° C. or more, but is preferably 100° C. to 170° C., more preferably 110° C. to 150° C., furthermore preferably 120° C. to 140° C. This temperature is a value obtained by measuring the temperature at the outlet of an extraction column in the case of using a pressure resistant extractor as a heating device and is a value obtained by measuring the temperature at the center of a pressure container in the case of using an autoclave as a heating device.

The pressure in the high-temperature heat treatment is not specifically limited, as long as it is a pressure over the atmospheric pressure, but is preferably 0.101 MPa to 0.79 MPa, more preferably 0.101 MPa to 0.60 MPa, furthermore preferably 0.101 MPa to 0.48 MPa.

The time of the high-temperature heat treatment is not specifically limited, as long as a treated material containing cycloaspartylglycine is obtained, but is preferably about 15 minutes to 600 minutes, more preferably about 30 minutes to 500 minutes, furthermore preferably about 60 minutes to 300 minutes.

Further, the conditions for the high-temperature heat treatment of the animal or plant-derived peptide is not specifically limited, as long as a treated material containing cycloaspartylglycine is obtained, but [temperature:pressure:time] is preferably [100° C. to 170° C.:0.101 MPa to 0.79 MPa:15 minutes to 600 minutes], more preferably [110° C. to 150° C.:0.101 MPa to 0.60 MPa:30 minutes to 500 minutes], furthermore preferably [120° C. to 140° C.:0.101 MPa to 0.48 MPa:60 minutes to 300 minutes].

The heat-treated product of animal or plant-derived peptide obtained may be subjected to treatment such as filtration, centrifugation, concentration, ultrafiltration, freeze drying, and powderization, as needed. Further, if a desired content of specific cycloaspartylglycine in the heat-treated product of animal or plant-derived peptide is not satisfied, other animal or plant-derived peptides, commercially available products, or synthetic products can be appropriately used and added to the specific cycloaspartylglycine that is insufficient.

1-3. Weight Ratio of Content of Glucose to Content of Maltose ([Glucose]/[Maltose] Weight Ratio) in Food or Beverage Product When the [glucose]/[maltose] weight ratio in the food or beverage product of the present invention is excessively low or high, it may be difficult to obtain the effect of reducing the astringent taste derived from cycloaspartylglycine. The [glucose]/[maltose] weight ratio in the food or beverage product of the present invention is 0.0050 or more, more preferably 0.010 or more, furthermore preferably 0.080 or more, particularly preferably 0.10 or more. Further, the upper limit of the [glucose]/[maltose] weight ratio in the food or beverage product of the present invention is 15 or less, preferably 10 or less, more preferably 7.0 or less, furthermore preferably 5.0 or less. Typically, the range of the [glucose]/[maltose] weight ratio in the food or beverage product of the present invention is 0.0050 to 15, preferably 0.010 to 10, more preferably 0.080 to 7.0, furthermore preferably 0.10 to 5.0.

Further, the contents of glucose and maltose in the food or beverage product of the present invention are not specifically limited, as long as the [glucose]/[maltose] weight ratio in the food or beverage product falls within the aforementioned ranges. Typically, the lower limit of the content of glucose in the food or beverage product of the present invention is 25 mg (25 mg/100 mL) or more, preferably 50 mg/100 mL or more, more preferably 350 mg/100 mL or more, furthermore preferably 460 mg/100 mL or more, with respect to 100 mL of the food or beverage product. Further, the upper limit of the content of glucose in the food or beverage product of the present invention is 5000 mg/100 mL or less, preferably 4550 mg/100 mL or less, more preferably 4250 mg/100 mL or less, furthermore preferably 4170 mg/100 mL or less. Typically, the content range of glucose in the food or beverage product of the present invention is 25 to 5000 mg/100 mL, preferably 50 to 4550 mg/100 mL, more preferably 350 to 4250 mg/100 mL, furthermore preferably 460 to 4170 mg/100 mL. Further, the lower limit of the content of maltose in the food or beverage product of the present invention is 200 mg/100 mL or more, preferably 450 mg/100 mL or more, more preferably 600 mg/100 mL or more, furthermore preferably 830 mg/100 mL or more. Further, the upper limit of the content of maltose in the food or beverage product of the present invention is 5500 mg/100 mL or less, preferably 4950 mg/100 mL or less, more preferably 4750 mg/100 mL or less, furthermore preferably 4540 mg/100 mL or less. Typically, the content range of maltose in the food or beverage product of the present invention is 200 to 5500 mg/100 mL, preferably 450 to 4950 mg/100 mL, more preferably 600 to 4750 mg/100 mL, furthermore preferably 830 to 4540 mg/100 mL.

The contents of glucose and maltose can be measured by a known method such as HPLC, LC-MS, GC-MS, LC, GC, and spectroscopy, e.g., near-infrared spectroscopy.

In the present invention, the method for adjusting the contents of glucose and maltose is not specifically limited, as long as the contents of glucose and maltose in the food or beverage product fall within the aforementioned ranges. For example, commercially available or synthetic products of glucose and maltose, and raw materials (such as food or beverage products and plants) containing glucose and maltose can be used. Further, only one of the commercially available or synthetic products of glucose and maltose, and the raw materials containing glucose and maltose can be used, or two or more of them can be also used in combination.

1-4. Relationship Between Content of Cycloaspartylglycine and [Glucose]/[Maltose] Weight Ratio In the food or beverage product of the present invention, the content of cycloaspartylglycine (mg/100 mL) (X) and the [glucose]/[maltose] weight ratio (Y) preferably satisfy $Y \leq 11.02 \times X^{-0.154}$ and $Y \geq 0.0255 \times X^{0.7454}$, more preferably $Y \leq 6.6445 \times X^{-0.091}$ and $Y \geq 0.49 \times X^{0.7837}$, for providing a food or beverage product having good taste while suppressing sharp astringent taste unique to cycloaspartylglycine in the food or beverage product.

1-5. Type of Food or Beverage Product

One embodiment of the present invention is a food or beverage product containing cycloaspartylglycine, glucose, and maltose, wherein a content of cycloaspartylglycine in the food or beverage product falls within a specific range and a [glucose]/[maltose] weight ratio in the food or beverage product falls within a specific range.

Preferable ranges of the content of cycloaspartylglycine and the [glucose]/[maltose] weight ratio are as described above, and a food or beverage product having good taste with sharp astringent taste unique to cycloaspartylglycine in the food or beverage product reduced can be obtained by adjusting the content of cycloaspartylglycine and the [glucose]/[maltose] weight ratio to the aforementioned ranges. Further, in the present invention, a food or beverage product with good balance between appropriate astringent taste unique to cycloaspartylglycine and sweetness derived from glucose, maltose, and the like can be achieved. In this description, "good balance between appropriate astringent taste unique to cycloaspartylglycine and sweetness derived from glucose, maltose, and the like" refers to a sensation with sharp astringent taste of cycloaspartylglycine reduced and with appropriate astringent taste unique to cycloaspartylglycine and sweetness derived from glucose, maltose, and the like balanced.

Further, it is confirmed that cycloaspartylglycine has TRPV1-stimulating activity and obesity-preventing and improving activity (PCT/JP2016/070639 and PCT/JP2016/070864), and the food or beverage product of the present invention can be a food or beverage product for stimulating TRPV1 and for preventing and improving obesity. Further, it also can be a food or beverage product with a display of a function relating to stimulation of TRPV1 and prevention and improvement of obesity.

The type of the food or beverage product of the present invention is not specifically limited, but examples thereof include foods, beverages, food/beverage compositions, food compositions, and beverage compositions. The food or beverage product of the present invention is preferably a beverage. Further, the type of beverage is not specifically limited but may be any one of carbonated beverages, non-carbonated beverages, alcohol beverages, non-alcohol beverages, tea beverages, nutrition beverages, and functional beverages. Preferable examples of the beverage in the present invention include tea beverages such as green tea, roasted green tea, blended tea, barley tea, Job's tears tea, mate tea, jasmine tea, black tea, oolong tea, du zhong tea, and Pu'er tea. In this description, "blended tea" means a mixture of a plurality of tea beverages such as barley tea and Job's tears tea.

1-6. Other Components

The food or beverage product of the present invention may contain various additives corresponding to the type of the food or beverage product other than the various components mentioned above. Examples of the various additives include sweeteners of saccharides other than above, acidulants, perfumes, vitamins, pigments, antioxidants, emulsifiers, preservatives, extracts, dietary fibers, pH adjusters, and quality stabilizers.

1-7. Food or Beverage Product Packaged in Container

The food or beverage product of the present invention may be packaged in a container after undergoing a step such as sterilization, as required. For example, a method of heat-sterilizing the food or beverage product after being packaged in a container or a method of sterilizing the food or beverage product and thereafter packaging it into a container in a sterile environment can be used.

The type of container is not particularly limited, and any one of containers generally used for food or beverage products such as resin containers including PET bottles, paper containers including paper packs, glass containers including glass bottles, metal containers including aluminum cans and steel cans, and aluminum pouches, for example, can be used.

2. Method for Producing Food or Beverage Product

According to an embodiment, the present invention is a method for producing a food or beverage product, the method comprising: step (a) of adding cycloaspartylglycine to adjust a content of cycloaspartylglycine in the food or beverage product to 0.0020 to 7.5 mg/100 mL; and step (b) of adding glucose and maltose to adjust a [glucose]/[maltose] weight ratio in the food or beverage product to 0.005 to 15. Further, the content of cycloaspartylglycine in the food or beverage product adjusted in step (a) above can be 0.0020 to 8.1 mg/100 mL, 0.0080 to 3.0 mg/100 mL, or 0.010 to 2.7 mg/100 mL. Further, the [glucose]/[maltose] weight ratio in the food or beverage product adjusted in step (b) above can be 0.010 to 10, 0.08 to 7.0, or 0.10 to 5.0.

The aforementioned production method can further comprise a step of adjusting the content of cycloaspartylglycine (mg/100 mL) (X) and the [glucose]/[maltose] weight ratio (Y) to satisfy $Y \leq 11.02 \times X^{-0.154}$ and $Y \geq 0.0255 \times X^{0.7454}$ or to satisfy $Y \leq 6.6445 \times X^{-0.091}$ and $Y \geq 0.49 \times X^{0.7837}$.

In the method for producing a food or beverage product of the present invention, the method for adjusting the content of cycloaspartylglycine and the method for adjusting the [glucose]/[maltose] weight ratio are not specifically limited, and it is possible to adjust the content and the weight ratio to the predetermined ranges, for example, by adding cycloaspartylglycine, glucose, and maltose. The method for adding cycloaspartylglycine, glucose, and maltose is not specifically limited, and commercially available products or synthetic products of cycloaspartylglycine, glucose, or maltose may be added, or raw materials containing cycloaspartylglycine, glucose, or maltose may be added, for example. The ranges of the contents of cycloaspartylglycine, glucose, and maltose and the ranges of the [glucose]/[maltose] weight ratio are as described above.

The type of food or beverage product produced in the present invention is not specifically limited, as described above, but the food or beverage product in the present invention is preferably a beverage. Examples thereof include tea beverages such as green tea, roasted green tea, blended tea, barley tea, Job's tears tea, mate tea, jasmine tea, black tea, oolong tea, du zhong tea, and Pu'er tea.

The method for producing a food or beverage product of the present invention can further comprise the steps of adding an additive or the like, which is generally contained in food or beverage products, and packaging the food or beverage product in a container. The types of additives and container are as described above, and a known method can be used as the packaging method in the container.

In the method for producing a food or beverage product of the present invention, the aforementioned various steps may be performed in any order, as long as the contents and the weight ratio of the food or beverage product finally obtained fall within the predetermined ranges.

3. Method for Reducing Sharp Astringent Taste of Cycloaspartylglycine in Food or Beverage Product According to an embodiment, the present invention is a method for reducing sharp astringent taste of cycloaspartylglycine in the food or beverage product, the method comprising: step (a) of adding cycloaspartylglycine to adjust a content of cycloaspartylglycine in the food or beverage product to 0.0020 to 7.5 mg/100 mL; and step (b) of adding glucose and maltose to adjust a [glucose]/[maltose] weight ratio in the food or beverage product to 0.005 to 15. Further, the content of cycloaspartylglycine in the food or beverage product adjusted in step (a) above can be 0.0020 to 8.1 mg/100 mL, 0.0080 to 3.0 mg/100 mL, or 0.010 to 2.7 mg/100 mL. Further, the [glucose]/[maltose] weight ratio in the food or beverage product adjusted in step (b) above can be 0.010 to 10, 0.08 to 7.0, or 0.10 to 5.0.

The aforementioned method can further comprise a step of adjusting the content of cycloaspartylglycine (mg/100 mL) (X) and the [glucose]/[maltose] weight ratio (Y) to satisfy $Y \leq 11.02 \times X^{-0.154}$ and $Y \geq 0.0255 \times X^{0.7454}$ or to satisfy $Y \leq 6.6445 \times X^{-0.091}$ and $Y \geq 0.49 \times X^{0.7837}$.

In the aforementioned method, the ranges of the contents of cycloaspartylglycine, glucose, and maltose and the ranges of the [glucose]/[maltose] weight ratio are as described above. Further, the method for adjusting the content of cycloaspartylglycine and the method for adjusting the [glucose]/[maltose] weight ratio are also as described above.

The type of the food or beverage product in the aforementioned method is not specifically limited, as described above, but the food or beverage product in the present invention is preferably a beverage. Examples thereof include tea beverages such as green tea, roasted green tea, blended tea, barley tea, Job's tears tea, mate tea, jasmine tea, black tea, oolong tea, du zhong tea, and Pu'er tea.

The aforementioned method can further comprise the steps of adding an additive or the like, which is generally contained in food or beverage products and a step of packaging the food or beverage product in a container. The types of additives and container are as described above, and a known method can be used as the packaging method in the container.

In the aforementioned method, the various steps may be performed in any order, as long as the contents and the weight ratio of the food or beverage product finally obtained fall within the predetermined ranges.

EXAMPLES

Hereinafter, the present invention will be described more specifically based on examples. The present invention is not limited to these examples.

Example 1: Evaluation of Influence of [Glucose]/[Maltose] Weight Ratio on Sharp Astringent Taste of Cycloaspartylglycine Sample beverages were prepared with the content of cycloaspartylglycine and the [glucose]/[maltose] weight ratio in the beverages variously changed, and the samples were each subjected to a sensory evaluation test. The method for preparing the sample beverages and the method of the sensory evaluation test are shown below.

<Sample Beverages 1 to 19>

Sample beverages 1 to 19 were prepared by mixing cycloaspartylglycine (stock solution concentration: 1 mg/mL), glucose (stock solution concentration: 100 mg/mL) and maltose (stock solution concentration: 100 mg/mL) so that the content of cycloaspartylglycine in each sample beverage was 0.00050, 0.0025, 0.010, 0.1, 2.7, 8.1, or 15 mg/100 mL, and the [glucose]/[maltose] weight ratio was 0, 0.010, 0.10, 1.0, 5.0, 10, or 30 in the sample beverage. Cycloaspartylglycine used was available from Carl Bechem GmbH and had a purity of >99%. Glucose and maltose used were available from NACALAI TESQUE, INC., were of standard first grade, and had a purity of >99%.

<Sample Beverages 20 to 23>

Sample beverages 20 to 23 were prepared by adding 0.2 g of a heat-treated product of soybean peptide (soybean extract), 0.2 g of a heat-treated product of tea peptide (tea extract), 0.05 g of a heat-treated product of collagen peptide (collagen extract), or 0.2 g of a heat-treated product of whey peptide (whey extract) to each sample beverage, and mixing glucose and maltose with each of the heat-treated product of peptides, so that the [glucose]/[maltose] weight ratio in the sample beverage was 1.0. The heat-treated products of various peptides were prepared by the following methods.

(1) Preparation of Heat-Treated Product of Soybean Peptide

The heat-treated product of soybean peptide used was obtained by treating soybean peptide with heat, followed by freeze drying. The heat-treated product of soybean peptide was produced by high-temperature high-pressure treatment of soybean peptide in a liquid. Specifically, about 15 ml of distilled water was added to 3 g of soybean peptide (Hinute A M, available from FUJI OIL CO., LTD.) and was put into an autoclave (available from TOMY SEIKO CO., LTD.), followed by high-temperature high-pressure treatment at 135° C. and 0.31 MPa for 3 hours. Thereafter, it was subjected to freeze drying to obtain a heat-treated product of soybean peptide (soybean extract) in powder form.

(2) Preparation of Heat-Treated Product of Tea Peptide

The first-picked tea leaves (variety: Yabukita, and total nitrogen: 6.3%) from Kagoshima was used as a plant. This tea was first subjected to pretreatment for reducing water-soluble proteins (three times of pre-extraction). That is, 200 g of hot water was added to 10 g of tea, followed by appropriate stirring and extraction for 5 minutes. After the completion of the extraction, filtration with a 140 mesh was performed to collect an extraction residue (tea residue). 200 g of hot water was poured onto the tea residue, followed by extraction for 5 minutes, to collect the tea residue. Again, extraction from the tea residue was performed in the same manner to collect the tea residue.

Thereafter, the tea (tea residue) subjected to the pre-extraction was degraded with an enzyme. 200 g of hot water at 50° C. was poured into the tea residue (total amount), and 1 g of protease (product name: PROTIN NY100, available from Daiwa Fine Chemicals Co. Ltd.) was added thereto, followed by reaction in a water bath at 55° C. for 3 hours under stirring (300 rpm) with a stirrer. Thereafter, it was held at 95° C. for 30 minutes to inactivate the enzyme.

The enzyme-treated solution was heated in the form of a tea liquid mixture without solid-liquid separation. The heat treatment was performed in an autoclave (available from TOMY SEIKO CO., LTD.) using a high-temperature high-pressure fluid at 135° C. for 3 hours. The solution after the treatment was filtered with a 140 mesh, to obtain a heat-treated product of tea peptide. Thereafter, it was subjected to freeze drying to obtain a heat-treated product of tea peptide (tea extract) in powder form.

(3) Preparation of Heat-Treated Product of Collagen Peptide

Collagen peptide (MDP1, available from Nippi, Incorporated) was added to distilled water to give 250 mg/mL and was put into an autoclave (available from TOMY SEIKO CO., LTD.), followed by high-temperature high-pressure treatment at 135° C. and 0.31 MPa for 10 hours, to obtain a heat-treated product of collagen peptide.

(4) Preparation of Heat-Treated Product of Whey Peptide 30 ml of distilled water was added to 3 g of whey peptide PeptigenIF-3090 (available from Arla Foods amba with an average molecular weight of 300 to 400), whey peptide with an average molecular weight of 440, or casein peptide CU2500A (available from Morinaga Milk Industry Co., Ltd. with an average molecular weight of 375) and was put into an autoclave (available from TOMY SEIKO CO., LTD.), followed by high-temperature high-pressure treatment at 135° C. and 0.31 MPa for 3 hours, to prepare a heat-treated product of whey peptide.

<Sample Beverages 24 to 28>

Sample beverages 24 to 28 were prepared by adding cycloaspartylglycine (chemically synthesized products) or heat-treated products of various peptides to a commercially available blended tea beverage. 0.1 mL of a cycloaspartylglycine solution with a stock solution concentration of 1 mg/mL was added, and 0.05 g or 0.2 g of the heat-treated products of various peptides prepared by the aforementioned methods were added thereto.

<Sensory Evaluation Test>

Sample beverages 1 to 28 were subjected to a sensory evaluation by three expert panelists. Specifically, scoring was performed by the expert panelists based on the following criteria, and the average scores are shown in Tables 1 to 3. Beverages with the average score of 3 or more were determined to be favorable.

(Criteria for Sensory Evaluation)

Score 5: Very favorably drinkable with no sharp astringent taste derived from cycloaspartylglycine sensed and good balance with sweetness.

Score 4: Favorably drinkable with little sharp astringent taste derived from cycloaspartylglycine sensed and good balance with sweetness.

Score 3: Drinkable with sharp astringent taste derived from cycloaspartylglycine remaining but good balance with sweetness.

Score 2: Difficult to drink with strong sharp astringent taste derived from cycloaspartylglycine and poor balance with sweetness.

Score 1: Undrinkable with very strong sharp astringent taste derived from cycloaspartylglycine.

Score 0: No problem with no sharp astringent taste sensed.

TABLE 1

| | Cyclo(Asp-Gly) (stock solution concentration: 1 mg/mL) (mL) | Glucose (stock solution concentration: 100 mg/mL) (mL) | Maltose (stock solution concentration: 100 mg/mL) (mL) | Water (mL) | Total amount (mL) | Concentration of Cyclo(Asp-Gly) (mg/100 mL) | Glucose/maltose weight ratio | Sensory evaluation score |
|---|---|---|---|---|---|---|---|---|
| 1 | 0.10 | 0 | 50 | 49.9 | 100 | 0.10 | 0 | 2 |
| 2 | 8.1 | 0 | 58 | 41.9 | 100 | 8.1 | 0 | 1 |
| 3 | 0.0025 | 0.5 | 49.5 | 50.0 | 100 | 0.0025 | 0.010 | 4 |
| 4 | 0.10 | 0.5 | 49.5 | 49.9 | 100 | 0.10 | 0.010 | 3 |
| 5 | 8.1 | 0.5 | 49.5 | 41.9 | 100 | 8.1 | 0.010 | 1 |

TABLE 1-continued

| | Cyclo(Asp-Gly) (stock solution concentration: 1 mg/mL) (mL) | Glucose (stock solution concentration: 100 mg/mL) (mL) | Maltose (stock solution concentration: 100 mg/mL) (mL) | Water (mL) | Total amount (mL) | Concentration of Cyclo(Asp-Gly) (mg/100 mL) | Glucose/maltose weight ratio | Sensory evaluation score |
|---|---|---|---|---|---|---|---|---|
| 6 | 0.010 | 4.6 | 45.4 | 50.0 | 100 | 0.010 | 0.10 | 4 |
| 7 | 2.7 | 4.6 | 45.4 | 47.3 | 100 | 2.7 | 0.10 | 3 |
| 8 | 15 | 4.6 | 45.4 | 35.0 | 100 | 15 | 0.10 | 1 |
| 9 | 0.0025 | 25 | 25 | 50.0 | 100 | 0.0025 | 1.0 | 5 |
| 10 | 0.1 | 25 | 25 | 49.9 | 100 | 0.1 | 1.0 | 5 |
| 11 | 8.1 | 25 | 25 | 41.9 | 100 | 8.1 | 1.0 | 3 |
| 12 | 0.00050 | 41.7 | 8.3 | 50.0 | 100 | 0.00050 | 5.0 | 0 |
| 13 | 0.010 | 41.7 | 8.3 | 50.0 | 100 | 0.010 | 5.0 | 5 |
| 14 | 2.7 | 41.7 | 8.3 | 47.3 | 100 | 2.7 | 5.0 | 4 |
| 15 | 0.0025 | 45.5 | 4.5 | 50.0 | 100 | 0.0025 | 10 | 4 |
| 16 | 0.10 | 45.5 | 4.5 | 49.9 | 100 | 0.10 | 10 | 3 |
| 17 | 8.1 | 45.5 | 4.5 | 41.9 | 100 | 8.1 | 10 | 2 |
| 18 | 0.10 | 48.4 | 1.6 | 49.9 | 100 | 0.10 | 30 | 2 |
| 19 | 8.1 | 48.4 | 1.6 | 41.9 | 100 | 8.1 | 30 | 1 |

TABLE 2

| | Contents of various extracts | Glucose (stock solution concentration 100 mg/mL) (mL) | Maltose (stock solution concentration 100 mg/mL) (mL) | Water (mL) | Total amount (mL) | Concentration of Cyclo(Asp-Gly) (mg/100 mL) | Glucose/maltose weight ratio | Sensory evaluation score |
|---|---|---|---|---|---|---|---|---|
| 20 | Heat-treated product of soybean peptide: 0.2 g | 25 | 25 | 50 | 100 | 0.1 | 1.0 | 5 |
| 21 | Heat-treated product of tea peptide: 0.2 g | 25 | 25 | 50 | 100 | 0.1 | 1.0 | 5 |
| 22 | Heat-treated product of collagen peptide: 0.05 g | 25 | 25 | 50 | 100 | 0.13 | 1.0 | 4 |
| 23 | Heat-treated product of whey peptide 0.2 g | 25 | 25 | 50 | 100 | 0.11 | 1.0 | 5 |

TABLE 3

| | Cyclo(Asp-Gly) (stock solution concentration: 1 mg/mL) or contents of various extracts | Blended tea (mL) | Total amount (mL) | Concentration of Cyclo(Asp-Gly) mg/100 mL) | Glucose/maltose weight ratio | Sensory evaluation score |
|---|---|---|---|---|---|---|
| 24 | Cyclo(Asp-Gly) stock solution: 0.1 ml | 99.9 | 100 | 0.1 | 0.96 | 5 |
| 25 | Heat-treated product of soybean peptide 0.2 g | 100 | 100 | 0.1 | 0.96 | 5 |
| 26 | Heat-teated product of tea peptide: 0.2 g | 100 | 100 | 0.1 | 0.96 | 5 |
| 27 | Heat-treated product of collagen peptide: 0.05 g | 100 | 100 | 0.13 | 0.96 | 4 |
| 28 | Heat-treated product of whey peptide: 0.2 g | 100 | 100 | 0.11 | 0.96 | 5 |

As shown in Table 1, it turned out that beverages with the content of cycloaspartylglycine and the weight ratio of glucose to maltose falling within the ranges of the present invention all had a sensory evaluation score of 3 or more and had excellent drinkability with sharp astringent taste unique to cycloaspartylglycine in the beverages reduced and good balance between appropriate astringent taste unique to cycloaspartylglycine and sweetness derived from glucose, maltose, and the like. Further, as shown in Table 2, the effects of the present invention could be obtained also in the case of using heat-treated products of various peptides to adjust the content of cycloaspartylglycine. Further, as shown in Table 3, the effects of the present invention could be obtained also in the case of adding chemically synthesized cycloaspartylglycine or heat-treated products of various peptides to a commercially available blended tea beverage to adjust the content of cycloaspartylglycine and the weight ratio of glucose to maltose. Accordingly, it was revealed that the present invention can achieve a food or beverage product having favorable taste with sharp astringent taste of cycloaspartylglycine reduced and further good balance between appropriate astringent taste unique to cycloaspartylglycine and sweetness derived from glucose, maltose, and the like by adjusting the content of cycloaspartylglycine in the food or beverage product and the weight ratio of glucose to maltose to the ranges of the present invention.

INDUSTRIAL APPLICABILITY

The present invention provides new means for preparing a food or beverage product having good taste with sharp astringent taste of cycloaspartylglycine in the food or beverage product reduced and therefore has high industrial applicability.

The invention claimed is:

1. A food or beverage product comprising cycloaspartylglycine, glucose, and maltose, wherein
a content of cycloaspartylglycine in the food or beverage product is 0.0020 to 7.5 mg/100 mL, and
a weight ratio of the content of glucose to the content of maltose ([glucose]/[maltose] weight ratio) in the food or beverage product is 0.005 to 15.

2. The food or beverage product according to claim 1, wherein the content of cycloaspartylglycine is 0.0080 to 3.0 mg/100 mL.

3. The food or beverage product according to claim 1, wherein the [glucose]/[maltose] weight ratio in the food or beverage product is 0.08 to 7.0.

4. The food or beverage product according to claim 1, wherein the content of cycloaspartylglycine (mg/100 mL) (X) and the [glucose]/[maltose] weight ratio (Y) in the food or beverage product satisfy $Y \leq 11.02 \times X^{-0.154}$ and $Y \geq 0.0255 \times X^{0.7454}$.

5. The food or beverage product according to claim 1, wherein the content of cycloaspartylglycine (mg/100 mL) (X) and the [glucose]/[maltose] weight ratio (Y) in the food or beverage product satisfy $Y \leq 6.6445 \times X^{-0.091}$ and $Y \geq 0.49 \times X^{0.7837}$.

6. The food or beverage product according to claim 1, wherein the cycloaspartylglycine is added as a heat-treated product of animal or plant-derived peptide.

7. The food or beverage product according to claim 6, wherein the heat-treated product of animal or plant-derived peptide is obtained from soybean peptide, tea peptide, whey peptide, or collagen peptide.

8. The food or beverage product according to claim 1, wherein the food or beverage product is a tea beverage.

9. The food or beverage product according to claim 8, wherein the food or beverage product is a blended tea beverage.

10. The food or beverage product according to claim 1, wherein the food or beverage product is packaged in a container.

11. A method for producing a food or beverage product, comprising:
step (a) of adding cycloaspartylglycine to adjust a content of cycloaspartylglycine in the food or beverage product to 0.0020 to 7.5 mg/100 mL; and
step (b) of adding glucose and maltose to adjust a weight ratio of the content of glucose to the content of maltose ([glucose]/[maltose] weight ratio) in the food or beverage product to 0.005 to 15.

12. The method according to claim 11, wherein the content of cycloaspartylglycine adjusted in step (a) is 0.0080 to 3.0 mg/100 mL.

13. The method according to claim 11, wherein the [glucose]/[maltose] weight ratio in the food or beverage product is 0.08 to 7.0.

14. A method for reducing sharp astringent taste of cycloaspartylglycine in a food or beverage product, comprising:
step (a) of adding cycloaspartylglycine to adjust a content of cycloaspartylglycine in the food or beverage product to 0.0020 to 7.5 mg/100 mL; and
step (b) of adding glucose and maltose to adjust a weight ratio of the content of glucose to the content of maltose ([glucose]/[maltose] weight ratio) in the food or beverage product to 0.005 to 15.

15. The method according to claim 14, wherein the content of cycloaspartylglycine adjusted in step (a) in the food or beverage product is 0.0080 to 3.0 mg/100 mL.

16. The method according to claim 14, wherein the [glucose]/[maltose] weight ratio in the food or beverage product is 0.08 to 7.0.

17. The food or beverage product according to claim 1, wherein a content of the glucose in the food or beverage product is 25 mg/100 ml to 5000 mg/100 ml; and a content of the maltose in the food or beverage product is 200 mg/100 ml to 5500 mg/100 ml.

18. The method according to claim 11, wherein a content of the glucose in the food or beverage product is 25 mg/100 ml to 5000 mg/100 ml; and a content of the maltose in the food or beverage product is 200mg/100 ml to 5500 mg/100 ml.

19. The method according to claim 14, wherein a content of the glucose in the food or beverage product is 25 mg/100 ml to 5000 mg/100 ml; and a content of the maltose in the food or beverage product is 200 mg/100 ml to 5500 mg/100 ml.

* * * * *